(12) United States Patent
Eelbode

(10) Patent No.: US 9,539,026 B2
(45) Date of Patent: Jan. 10, 2017

(54) NEEDLE GUIDE AND METHOD FOR DETERMINING THE POSITION OF A NEEDLE

(71) Applicant: MEPY BENELUX BVBA, Ostend (BE)

(72) Inventor: Nico Eelbode, Menlo Park, CA (US)

(73) Assignee: TELEFLEX MEDICAL EUROPE LTD., Athlone (IE)

( * ) Notice: Subject to any disclaimer, the term of this patent is extended or adjusted under 35 U.S.C. 154(b) by 166 days.

(21) Appl. No.: 13/977,518

(22) PCT Filed: Oct. 11, 2012

(86) PCT No.: PCT/US2012/002012
§ 371 (c)(1),
(2) Date: Jun. 28, 2013

(87) PCT Pub. No.: WO2013/054168
PCT Pub. Date: Apr. 18, 2013

(65) Prior Publication Data
US 2014/0228685 A1    Aug. 14, 2014

(30) Foreign Application Priority Data
Oct. 12, 2011   (BE) .................... 2011/0598

(51) Int. Cl.
*A61B 17/34*   (2006.01)
*A61B 8/08*   (2006.01)
*A61B 90/00*   (2016.01)

(52) U.S. Cl.
CPC .......... *A61B 17/3403* (2013.01); *A61B 8/0841* (2013.01); *A61B 2017/3413* (2013.01); *A61B 2090/062* (2016.02)

(58) Field of Classification Search
None
See application file for complete search history.

(56) References Cited

U.S. PATENT DOCUMENTS

| | | | |
|---|---|---|---|
| 4,576,175 A | 3/1986 | Epstein | |
| 5,100,387 A | 3/1992 | Ng | |
| 5,235,987 A * | 8/1993 | Wolfe | A61B 8/0833 600/461 |
| 5,660,185 A * | 8/1997 | Shmulewitz et al. | 600/562 |
| 6,639,544 B2 * | 10/2003 | Yamada | G01D 5/145 338/12 |
| 2002/0156376 A1 * | 10/2002 | Wang et al. | 600/439 |

(Continued)

FOREIGN PATENT DOCUMENTS

| | | |
|---|---|---|
| EP | 0 025 214 | 3/1981 |
| GB | 2 130 726 | 6/1984 |

(Continued)

*Primary Examiner* — Long V Le
*Assistant Examiner* — Marjan Saboktakin
(74) *Attorney, Agent, or Firm* — Baker & Hostetler LLP

(57) ABSTRACT

A needle guide includes an attachment means for attachment to an imaging probe that forms an image of an area, a fixed part, and a movable part movable at an angle. The movable part includes one or more needle guide elements that receive a needle in a guiding manner, and at least one rotation sensor to measure the angular rotation of the movable part. A method for determining the position of a needle attached to the needle guide relative to the imaging probe is also disclosed.

17 Claims, 4 Drawing Sheets

(56) References Cited

U.S. PATENT DOCUMENTS

| | | | |
|---|---|---|---|
| 2007/0221110 A1* | 9/2007 | Hillenbrand | D05B 55/14 112/226 |
| 2009/0062831 A1* | 3/2009 | Teichert et al. | 606/189 |
| 2010/0041990 A1* | 2/2010 | Schlitt | A61B 17/3403 600/439 |
| 2011/0245659 A1* | 10/2011 | Ma | A61B 5/066 600/424 |

FOREIGN PATENT DOCUMENTS

| | | |
|---|---|---|
| WO | WO 02/00276 | 1/2002 |
| WO | WO 2005/094934 | 10/2005 |

* cited by examiner

NEEDLE GUIDE AND METHOD FOR DETERMINING THE POSITION OF A NEEDLE

CROSS-REFERENCE TO RELATED APPLICATIONS

This application is a National Stage Application of International Patent Application No. PCT/IB2012/002012, filed on Oct. 11, 2012, which claims priority to foreign Belgian Patent Application No. BE 2011/0598, filed on Oct. 12, 2011, the disclosures of which are incorporated by reference in their entirety.

FIELD OF THE INVENTION

This invention relates to a needle guide comprising attachment means to attach this needle guide to an imaging probe which is provided to produce an image of an area, wherein the needle guide comprises a fixed part which, in the mounted condition, is set up in a fixed manner in relation to the imaging probe, and wherein the needle guide comprises a part which is movable at an angle in relation to the fixed part, wherein this movable part comprises one or more needle guide elements to insert a needle in a guiding manner according to the area.

This invention similarly relates to a method for determining the position of a needle, which is attached movably in a needle guide of this type to an imaging probe, in relation to this imaging probe.

More specifically, this invention offers a solution for the insertion of a needle using a transducer of an echoscope. However, this invention could also be used in other imaging probes.

BACKGROUND

Echography is a technology which uses sound waves. With this technology, organs or an unborn child, inter alia, can be visualised. Applications also exist outside medical science.

Sound waves are transmitted into the body of a human or animal using a transducer. The sound waves reflected by the body are picked up on return by the same transducer and converted into an electrical voltage. The electrical signals are converted using a computer system into video images, which are visualised on a monitor of the echoscope.

In a plurality of applications in which an echoscope is used, the localisation of a needle is important. This applies in the case of the piercing of blood vessels, the guiding of a puncture needle in the case of, for example, amniotic fluid punctures or biopsies, in the insertion of catheters for ablation, for drainage, access to blood vessels, anaesthesia such as, for example, a local anaesthetic wherein a plexus is surrounded by anaesthesia via a puncture, etc. All manner of treatments wherein a body is pierced with needles such as occupational therapy, microwaves and radio frequency can also use echography with localisation.

A needle of this type is often inserted with a free hand, wherein the zone to be pierced is visualised using the echoscope and a check is carried out during the piercing to ensure that the needle is correctly inserted. However, the insertion of a needle with the free hand requires a certain dexterity and experience in order to insert the needle with reasonable accuracy. Only if the needle has actually pierced will it appear or not appear in the image of the zone visualised using the transducer and the echoscope. If it is established that the needle is not in the area of the echoscope or near the zone to be pierced, the piercing must often be repeated several times. However, more than one piercing causes discomfort to the patient and additional piercing damage, and may, in the case of the piercing of tumours, even be fatal.

To overcome this problem, needle guides have been developed with which the needles are guided so that it is certain that the needle is inserted into the area which is visualised with the echoscope and the transducer. A needle guide of this type is positioned on a holder which is fitted to the transducer. With the first needle guides, however, only a needle with a specific diameter could be inserted at a specific angle into the body.

Systems with needle guides already exist, wherein the angle at which a needle is inserted into a body can be determined step-by-step, according to the area which is visualised. In needle guides of this type, the needle can be brought at different predefined angles into the area visualised with the echoscope. It is already possible to visualise these predefined angles on the monitor of the echoscope. By positioning the transducer, wherein the zone of the body to be pierced is visualised, wherein the different possible angles for piercing are also visualised, the angle for piercing which produces the best result can be selected. However, this system still has a limited accuracy, so that the desired result is often not immediately achieved with the piercing, which must then be repeated several times. As already mentioned, more than one piercing causes discomfort to the patient and additional piercing damage, and may, in the case of the piercing of tumours, even be fatal.

Systems already exist wherein the needle can be displaced in a stepless manner in an area using the needle guide, and the position of the needle can nevertheless be accurately determined. These systems use magnetic localisation, known as GPS systems. A clamp, to which the guide is fitted, is positioned on the transducer. Accurate localisation of the needle is possible with a magnet and a plurality of sensors. One sensor is positioned on the clamp, another on or in an ancillary needle or on a standard sterile needle. The angle at which the ancillary needle or the standard sterile needle is inserted into the body can be determined using the sensors. The predicted angle at which the ancillary needle enters the body is displayed on the monitor. However, the use of an ancillary needle has the disadvantage that the ancillary needle has a larger diameter than the actual needle with which the treatment is to be carried out, so that the actual needle (possibly following removal of the sensor, if this had been inserted into the ancillary needle) can be inserted through the ancillary needle into the body. The use of ancillary needles is furthermore expensive. Both in the case of the use of an ancillary needle and in the case of systems wherein a sensor is attachable directly to a standard sterile needle, the magnet and associated sensors for a magnetic location determination of this type are fairly expensive. If the sensor is positioned on or in the needle, this must also be sterile. In these systems, a new sterile sensor and (if ancillary needles are used) a new sterile ancillary needle are normally used for each treatment. In this way, a treatment costs a lot of money. If ancillary needles with larger diameters are used, much more damage is furthermore caused than if only the actual needles with the necessary diameter are applied.

SUMMARY

This object of the invention is achieved by providing a needle guide comprising attachment means to attach this needle guide to an imaging probe which is provided to produce an image of an area, wherein the needle guide comprises a fixed part which, in the mounted condition, is set up in a fixed manner in relation to the imaging probe, and wherein the needle guide comprises a part which is movable at an angle in relation to the fixed part, wherein this movable part comprises one or more needle guide elements to insert a needle in a guiding manner according to the area, and wherein this needle guide comprises at least one rotation sensor to measure the angular rotation of the movable part in relation to the fixed part.

The rotation sensor is mounted on the guide rather than on or in the needle, as in the case of current magnetic localisation methods. A rotation sensor of this type then no longer needs to be set up in the sterile zone and is therefore also usable more than once, thereby ensuring a considerable cost price reduction. Special (expensive) ancillary needles are also no longer possible, but the actual needle can be inserted directly into the body using the needle guide in order to pierce the required zone. Using the measured angular rotation, the prediction can be visualised relating to where the needle would end up if it were moved further in the one or more needle guide elements towards the human or animal. The user then also knows precisely where the needle will end up and must therefore only perform one piercing.

In a more specific embodiment, the imaging probe of a needle guide according to this invention is a transducer of an echoscope.

The rotation sensor of a needle guide according to this invention is preferably at least partially disposed on the movable part of the needle guide.

In a preferred embodiment of a needle guide according to this invention, the rotation sensor is an electrical sensor.

Rotation sensors can operate on the basis of electrical, magnetic or optical effects. The use of electrical sensors can provide simpler, more economical embodiments. Alternatively, but less preferably, magnetic sensors can also be used, such as, for example an LVDT sensor (Linear Variable Differential Transformer) as a rotation sensor.

However, even more preferably, the rotation sensor of the needle guide according to the invention is a potentiometer.

A potentiometer of this type is a form of electrical sensor and is an example of an analogue transducer. The use of potentiometers of this type ensures particularly simple and economical embodiments of needle guides according to this invention. It is thus again possible to provide a disposable item in an affordable manner, wherein the sensors are no longer reused and the cost price per treatment nevertheless remains relatively limited.

Alternatively, but less preferably, it would also be possible to use a digital transducer such as, for example, a displacement encoder. Both absolute and incremental displacement encoders could be used for this purpose. With an incremental displacement encoder, a wheel, for example, is used, wherein the rotations of the wheel are counted with a revolution counter (e.g. impulse counter).

A specific embodiment of a needle guide according to this invention additionally comprises at least one displacement sensor to measure the displacement of a needle which is disposed movably in the one or more needle guide elements in relation to these one or more needle guide elements.

In addition to the prediction of where the needle would end up if it were moved further in the one or more needle guide elements towards the human or animal, the correct position of the point of the needle can also thus be visualised. In this way, needles which are visualised less well immediately due to their reflection properties can nevertheless be visualised with certainty.

Such a displacement sensor of a needle guide according to the invention is preferably also at least partially disposed on the movable part.

In a preferred needle guide according to this invention with a displacement sensor of this type, this displacement sensor is an electrical sensor.

Even more preferably, this displacement sensor is a potentiometer.

The object of this invention is furthermore also achieved by providing a method for determining the position of a needle, which is attached movably in a needle guide to an imaging probe, in relation to this imaging probe, wherein this method comprises the provision of a needle guide according to this invention and comprises the measurement of the angular rotation of the movable part in relation to the fixed part using the rotation sensor.

In a more specific method according to this invention, a needle guide according to this invention is provided with a displacement sensor and the displacement of the needle in relation to the one or more needle guide elements is measured using the displacement sensor.

Preferably, in a method according to this invention, wherein the imaging probe is a transducer of an echoscope:
  an image of a part of a human or an animal to be pierced with the needle is produced using the echoscope and the transducer;
  on the basis of the measured angular rotation, a prediction is made of the direction in which the needle would pierce the human or animal in the event of further displacement of the needle via the one or more needle guide elements towards the human or animal and/or the position of the end of the needle is determined on the basis of the measured displacement;
  and this predicted direction and/or this determined position of the end of the needle is displayed on the image.

In a specific embodiment according to this invention, in a method of this type, the image produced using the transducer and the echoscope of the part of the human or animal to be pierced is read out from the echoscope and the predicted direction and/or the determined position is/are superimposed on this image.

The superimposition of an image of this type on a different image is known as the overlay technique. The direction and/or the position of the end of the needle are positioned with a transparent background at the top of the image of the echoscope.

This image with the predicted direction and/or the determined position superimposed is furthermore even more specifically read back into the echoscope and visualised using the echoscope in order to display the predicted direction and/or the determined position on the image.

In a particular embodiment of a method according to this invention, two lines are visualised on either side next to the predicted direction in order to display the predicted direction on the image.

This invention is now explained in detail with reference to the following detailed description of a number of preferred embodiments of needle guides and methods according to this invention. The purpose of this description is exclusively to provide illustrative examples and to indicate further advantages and special features of this invention, and may therefore in no way be interpreted as a limitation of the scope of application of the invention or of the patent rights asserted in the claims.

BRIEF DESCRIPTION OF THE DRAWINGS.

In this detailed description, reference numbers are used to refer to the drawings attached hereto, in which.

DETAILED DESCRIPTION

Figure 1A:
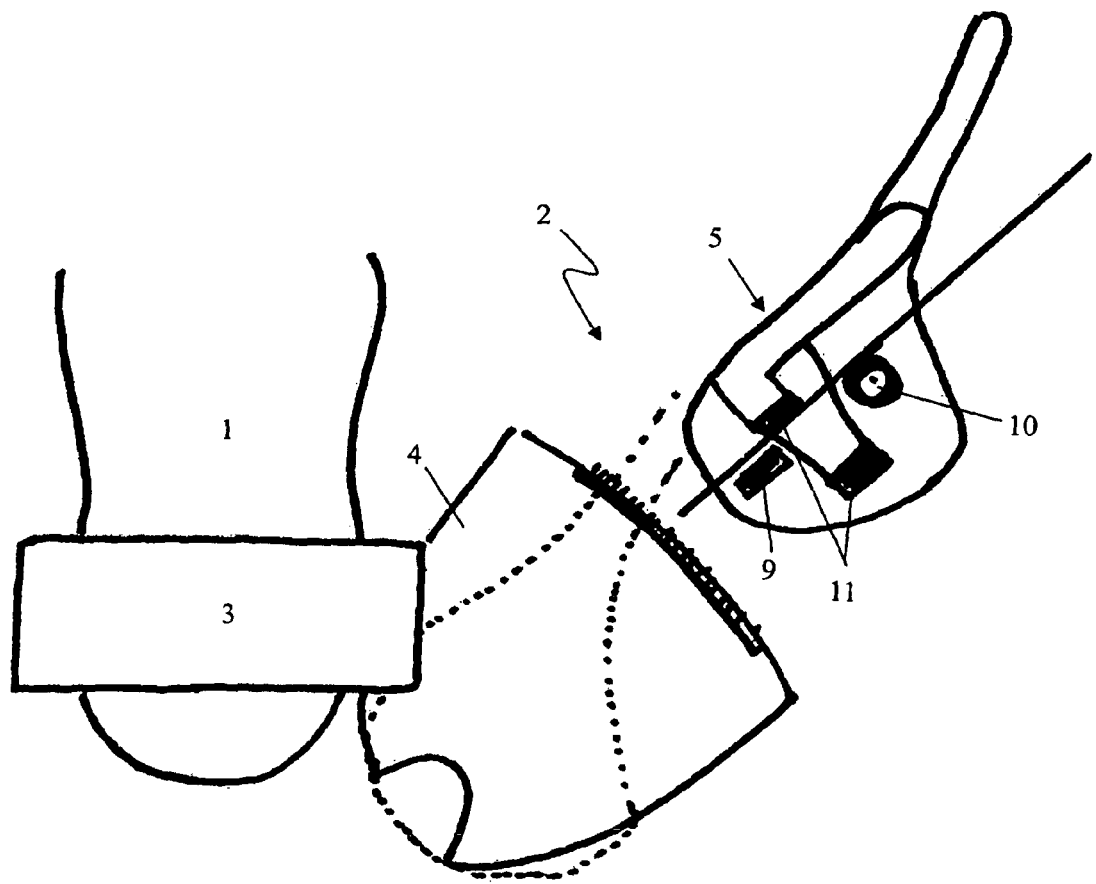
FIG. 1a shows a diagram of an embodiment of a needle guide according to the invention, attached to a transducer of an echoscope, with the displaceable part of the needle guide detached from the fixed part.
Figure 1B:
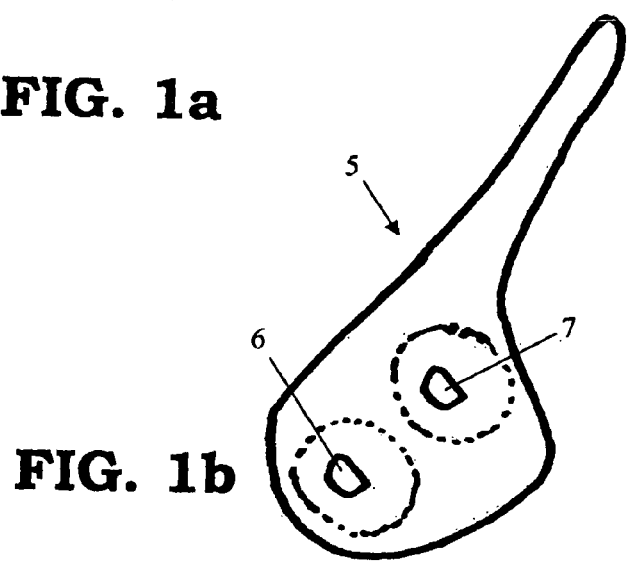
FIG. 1b shows a diagram of the displaceable part of the needle guide from FIG. 1a, with the rotation sensor and the displacement sensor which are located on the rear side, shown on the front side, instead of the needle guide elements.
Figure 2:
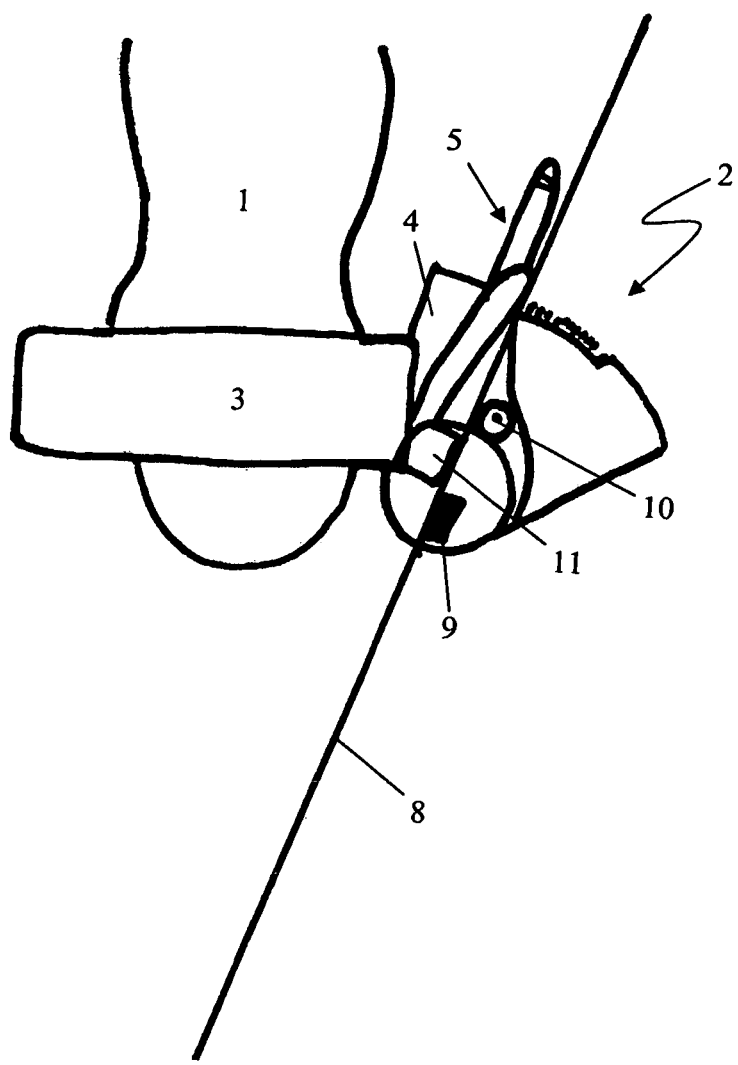
FIG. 2 shows a diagram of the embodiment of the needle guide from FIG. 1a, attached to a transducer of an echoscope, with the displaceable part of the needle guide attached to the fixed part and with a needle inserted between the needle guide elements at a first angle in relation to the transducer.
Figure 3:
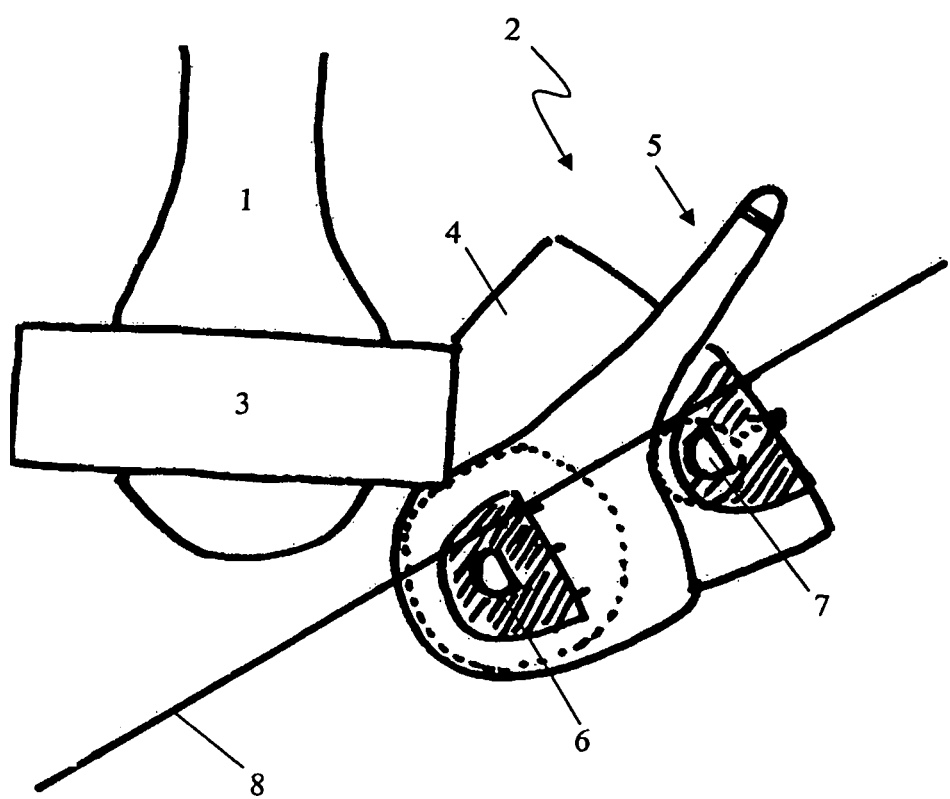
FIG. 3 shows a diagram of the embodiment of the needle guide from FIG. 1a, attached to a transducer of an echoscope, with the displaceable part of the needle guide attached to the fixed part, with a needle inserted between the needle guide elements at a second angle in relation to the transducer and with the rotation sensor and the displacement sensor which are located on the rear side, shown on the front side, instead of the needle guide elements.
Figure 4:
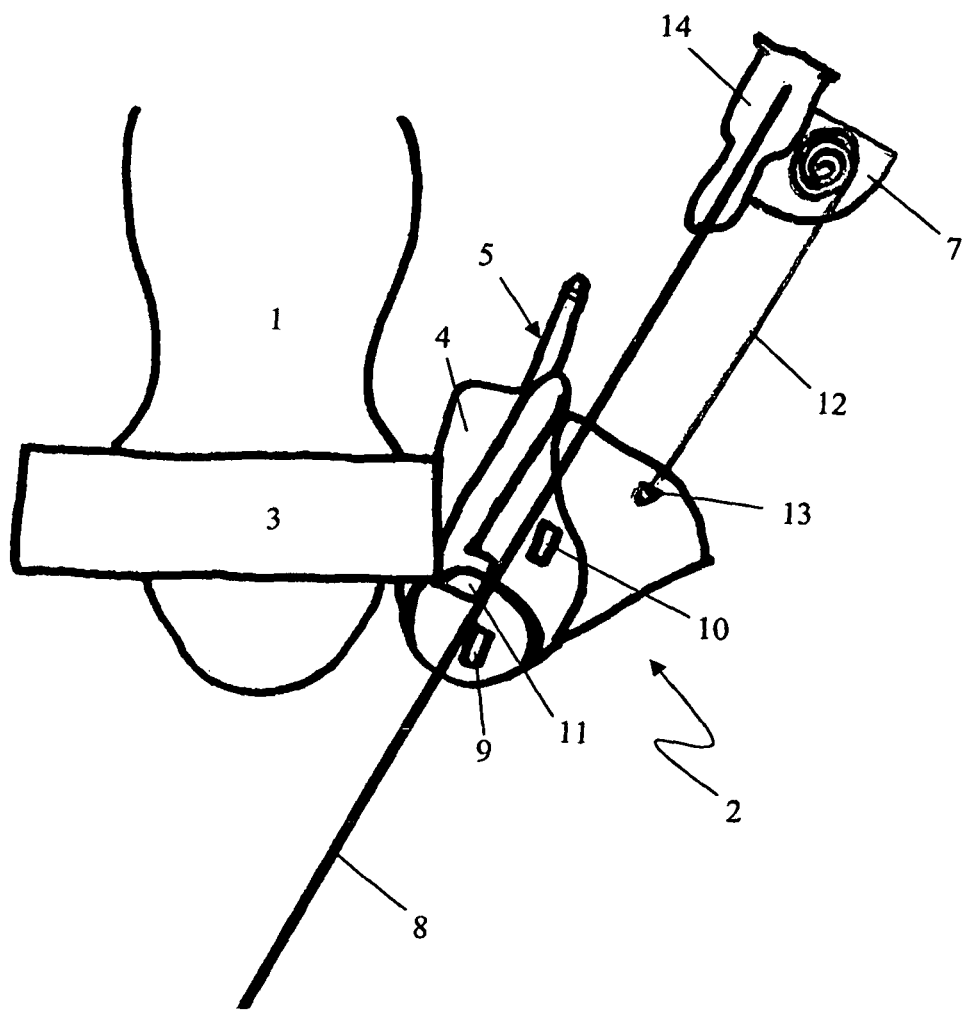
FIG. 4 shows a diagram of a second embodiment of a needle guide according to the invention with an alternative displacement sensor, attached to a transducer of an echoscope, with the displaceable part of the needle guide attached to the fixed part and with a needle inserted between the needle guide elements.

FIGS. 1a to 4 show a number of possible embodiments of a needle guide (2) according to this invention. The needle guide (2) in each case comprises a fixed part (4) and a movable part (5). The movable part (5) is detachably attachable to the fixed part (4), so that both are separately sterilisable if necessary. In the attached condition, as shown in FIGS. 2 to 4, the movable part (5) is movable in a hinged manner in relation to the fixed part (4). The fixed part (4) of the needle guide (2) is in each case detachably attachable to a clamp (3). This clamp (3) is in turn detachably attachable to a transducer (1) of an echoscope. In the figures, the fixed part (4) is in each case attached to the clamp (3) and the clamp is in each case attached to the transducer (1). It goes without saying that, as is already known, there are many different possible ways to provide the clamp (3) attachable to the transducer (1), to provide the fixed part (4) attachable to the clamp (3), and to provide the movable part (5) displaceable in a hinged manner on the fixed part (4).

In needle guides (2) of this type, the needle (8) is inserted into the movable part (5) of the needle guide (2) using needle guide elements (9, 10, 11). In the embodiment shown in FIGS. 1a to 3, the needle guide elements (9, 10, 11) consist of a fixed guide element (9), a rotatable axis (10) and a spring-loaded clamp (11). In the embodiment shown in FIG. 4, the needle guide elements (9, 10, 11) consist of two fixed guide elements (9, 10) and a spring-loaded clamp (11). Thanks to the spring-loaded clamp (11), needles with different diameters can be clamped in each case between the needle guide elements (9, 10, 11). Alternatively, but less preferable, as already known in the prior art, the needle guide elements may, for example, also consist of one or more grooves which are disposed in the movable part (5) of the needle guide (2). Different grooves are then preferably provided to apply needles with different corresponding diameters. Due to the hinged movement of the movable part (5) in relation to the fixed part (4) of the needle guide (2), the angle of the needle (8) in relation to the transducer (1) can be set in a stepless manner.

Furthermore, the needle guides (2) shown in each case comprise two sensors (6, 7). In the embodiments shown, these two sensors (6, 7) in each case comprise rotary potentiometers. Potentiometers (6, 7) have a fixed component and a mechanically movable component. If the movable component is displaced, the variable resistance of the potentiometer changes, so that this variable resistance is a parameter which corresponds to the displacement. In a rotary potentiometer, the movable component is displaced through rotation.

The first potentiometer (6) of the needle guides (2) in each case measures the angular rotation of the fixed part (4) in relation to the movable part (5), whereas the second potentiometer (7) measures the displacement of the end (the point) of the needle (8).

In the first potentiometer (6, 7), the fixed component and the displaceable component are each attached to a different part (fixed part (4) and movable part (5)) of the needle guide (2). The angle at which the needle (8) will be inserted into the body using the needle guide (2) can be determined by means of the position of the imaging probe (1), the position of the clamp (3) on the imaging probe (1), and the position of the fixed part (4) of the needle guide (2) on the clamp (3).

In the second potentiometer (7) from the first embodiment, as shown in FIGS. 1a to 3, the fixed component of the potentiometer (7) is permanently attached to the movable part (5) of the needle guide (2), whereas the displaceable component is attached to the rotatable axis (10). In the event of displacement of the needle (8), the rotatable axis (10) rotates and the displaceable component of the potentiometer (7) is displaced in relation to the fixed component of this potentiometer (7), so that the resistance change of the potentiometer (7) is a measure of the displacement of the point of the needle (8). In this way, the second potentiometer (7) can determine the length which the part of the needle (8) has which ends up in the body. When the needle (8) is inserted, a zero position of the point of the needle (8) must of course be determined via a calibration.

In the second potentiometer (7) from the second embodiment, as shown in FIG. 4, the fixed component of the potentiometer (7) is located on a part of the potentiometer (7) which is detachably attachable to the handle (14) of the needle (8). The displaceable component comprises a rewindable wire (12), one end of which is rewindable level with the fixed component on the part of the potentiometer (7) which is detachably attachable to the handle (14). The other end of this rewindable wire (12) is permanently attached (13) to the movable part (5) of the needle (2). Alternatively, this end could also be attached to the fixed part (4) of the needle (2). In the event of displacement of the needle (8), the wire (12) is unwound and the displaceable component of the potentiometer (7) is displaced in relation to the fixed component of this potentiometer (7), so that the resistance change of the potentiometer (7) is a measure of the displacement of the point of the needle (8). In this way, the second potentiometer (7) can determine the length which the part of the needle (8) has which ends up in the body. When the needle (8) is inserted, a zero position of the point of the needle (8) must of course be determined via a calibration. The potentiometer (7) furthermore comprises a spring to wind the rewindable wire (12) back up. In such an embodiment of a needle guide (2) according to the invention with a potentiometer (7) of this type with a rewindable wire, this second potentiometer (7) must be sterile. However, the cost price of potentiometers (7) of this type is considerably lower than the cost price of the necessary sensors for the systems from the prior art, so that the provision of a sterile potentiometer (7) of this type per treatment is in fact affordable. In order to provide a potentiometer (7) of this type, either a string potentiometer can be used which is available as standard on the market or a more conventional potentiometer, supplemented with a rewindable wire with a spring-back mechanism.

By means of software, both the angle which the needle (8) forms in relation to the transducer (1), and therefore also in relation to the image which is formed with this transducer (1), and the position of the point of the needle (8) can be determined in each case via the two potentiometers (6, 7), and this can be displayed on the image formed with the transducer (1) on a screen (not shown here), for example using a line which indicates the angle and a marker symbol, such as, for example, a dot or a cross on the line, which visualises the tip of the needle (8). Consequently, the user knows with this invention where the needle (8) will precisely end up for the insertion of the needle (8). Instead of a line which indicates the angle, two lines can also be used on the monitor to show the angle between which the needle (8) will precisely be located. If two lines are used parallel with the line where the needle (8) will end up, the inserted needle (8) can then also itself be visualised unhindered on the screen.

These new techniques can be used not only in new echographs which are adapted to read in the signals from new sensors (6, 7) and convert them into the lines which are additionally displayed on the monitor (in addition to the image which is formed with the transducer (1)), but also on all existing echographs by, for example, reading out and digitising the video image from the echograph, by reading in and processing the signals from the sensors (6, 7) with an additional electronic unit, and by programming screen overlay software with which the line(s) can then be added to the digitised video image, so that the lines can then be displayed on this video image in superimposed form. This video image with overlay can also be read back into the existing echograph, which can then display the entire image on the monitor.

The invention claimed is:

1. A needle guide, comprising:
a coupler;
a fixed part having a conical shape configured to be fixedly mounted to an imaging probe via the coupler, the fixed part having a hollow conical cavity with an open proximal end and a round distal end defining an opening configured to allow a needle to pass therethrough, wherein the opening in the round distal end is smaller than the open proximal end;
a movable part configured to be at least partially received within the hollow conical cavity of the fixed part, the movable part defining a second cavity for receiving the needle, wherein the movable part comprises one or more needle guide elements within the movable part, wherein the one or more needle guide elements comprising:
a fixed needle guide element,
a resilient needle guide element, and
a rotatable element;
at least one rotation sensor configured to measure an anaular rotation of the movable part relative to the fixed part; and
at least one displacement sensor configured to attach to the rotatable element and to measure displacement of the needle relative to the movable part.

2. The needle guide of claim 1, wherein the rotation sensor is at least partially disposed on the movable part.

3. The needle guide of claim 1, wherein the rotation sensor is an electrical sensor.

4. The needle guide of claim 3, wherein the rotation sensor is a potentiometer.

5. The needle guide of claim 1, wherein the displacement sensor is disposed at least partially on the movable part.

6. The needle guide of claim 1, wherein the displacement sensor is an electrical sensor.

7. The needle guide of claim 6, wherein the displacement sensor is a potentiometer.

8. A method for determining a position of a needle movable in a needle guide relative to an imaging probe, the method comprising:
provisioning the needle guide of claim 1;
measuring an angular rotation of the movable part relative to the fixed part using the at least one rotation sensor; and
measuring a displacement of the needle relative to the movable part using the at least one displacement sensor.

9. The method of claim 8, wherein the imaging probe is a transducer of an echoscope, the method further comprising:
imaging a part of a human or an animal to be pierced with the needle using the transducer of the echoscope;
predicting, based on the measured angular rotation, a direction in which the needle would pierce the human or the animal following displacement of the needle via the one or more needle guide elements within the human or the animal;
determining a position of a tip of the needle based on the measured displacement of the needle relative to the movable part; and
displaying the predicted direction and the determined position of the tip of the needle on the image.

10. The method of claim 9, wherein displaying the predicted direction and the determined position of the tip of the needle on the image comprises superimposing the predicted direction and the determined position of the tip of the needle on the image.

11. The method of claim 10, wherein superimposing the predicted direction and the determined position of the tip of the needle on the image comprises transmitting the predicted direction and the determined position of the tip of the needle to the echoscope and displaying, using the echoscope, the predicted direction and the determined position of the tip of the needle on the image.

12. The method of claim 11, wherein displaying the predicted direction and the determined position of the tip of the needle on the image comprises displaying two lines on either side of an image of the needle to display the predicted direction on the image.

13. The needle guide of claim 1, wherein the resilient needle guide element is a spring-loaded clamp that is configured to enable the one or more needle guide elements to guide needles of different diameters.

14. The needle guide of claim 1, wherein the coupler is detachably connected to the imaging probe and the fixed part.

15. The method of claim 11, wherein displaying the predicted direction and the determined position of the tip of the needle on the image comprises displaying a visual indicator at the tip of the image of the needle on the image.

16. The needle guide of claim 1, wherein the portion of the movable part received within the hollow conical cavity of the fixed part has a shape complementary to the hollow conical cavity.

17. The needle guide of claim 1, wherein the one or more needle guide elements further comprise a second fixed needle guide element.

* * * * *